United States Patent [19]

Holmqvist et al.

[11] 4,240,691

[45] Dec. 23, 1980

[54] PROTECTIVE DEVICE FOR OPTICAL ELEMENTS

[75] Inventors: Göran Holmqvist, Älvsjö; Staffan Källén, Johanneshov; Bertil Jansson, Täby, all of Sweden

[73] Assignee: AGA Aktiebolag, Lidingo, Sweden

[21] Appl. No.: 37,043

[22] Filed: May 8, 1979

[30] Foreign Application Priority Data

Jun. 15, 1978 [SE] Sweden ............................... 7806890

[51] Int. Cl.³ .................................................. G02B 7/00
[52] U.S. Cl. .................................. 350/63; 15/250.01; 134/199
[58] Field of Search ................ 350/63, 319; 15/250.01; 134/199

[56] References Cited

U.S. PATENT DOCUMENTS

| 3,516,723 | 6/1970 | Guier | 350/63 |
| 3,565,516 | 2/1971 | Thomas et al. | 350/63 |
| 3,725,028 | 4/1973 | Cramer | 350/63 |

*Primary Examiner*—Jon W. Henry
*Attorney, Agent, or Firm*—Larson, Taylor and Hinds

[57] ABSTRACT

A device for keeping an outer surface of an optical element clean, said element being located in surroundings where deposits can be quickly formed on said element. The device has a protective device or screen with an opening placed in front of the surface to be protected. This opening has inner walls extending out from said surface of the optical element. The screen has a slot, which extends peripherally around the edge of the opening facing the surface to be protected, and gas is forced to stream through the slot. At least a part of the inner surface of the opening has an inwardly projecting part having a surface remote from the optical element which is parallel to or inclined outwardly from a symmetrical plane through the element.

7 Claims, 5 Drawing Figures

PROTECTIVE DEVICE FOR OPTICAL ELEMENTS

BACKGROUND OF THE INVENTION

1. Field of the Invention

The present invention relates to a device which is arranged to be placed in front of a relatively large surface of an optical element of an instrument, which is located in a dusty environment where settling of the dust readily occurs, said surface of the optical element being exposed to the surrounding atmosphere and said device being intended to keep said surface clean.

2. Brief Description of the Prior Art

Nowadays, an increasingly extensive use is made of optical instruments, such as TV-cameras and optical instruments working within the infrared wavelength region. Particularly, such instrumentation is used more and more for supervising purposes, a TV-camera or an IR-camera being arranged to monitor and register selected changes in the course of events, currently and over a long period of time, which changes in some cases can be controlled by the registration result. However, prior to the present invention, it has been difficult to use instruments of this kind in surroundings where deposits of dust and soot are bound to occur, or in gasfilled and/or damp atmosphere, since the surface of the outermost component of the optical system in the instrument, very often a protecting window, very quickly becomes covered with an opaque layer.

Experiments have earlier been made to solve this problem, by placing a tube in front of the surface of the outermost optical element and by blowing gas in a direction away from said optical element, in order to prevent dust and dirt from impinging up and settling on the surface of the element. The experiments have shown that the tube must be very long in relation to its cross-sectional area, in order to obtain a laminar gas stream therefrom. A laminar stream is essential, since otherwise turbulent flows in the tube will bring dust and dirt into contact with the surface to be kept clean. When there is a demand for a wide view-angle there are, however, contradictory demands on the tube and hence the provision of such a tube is not always a solution to the problem.

Attempts have also been made to solve this serious problem by redrafting the optical properties of the isntruments to be used in such a way, that the front surface of the system is made as small as possible, since it is easier to keep a small surface clean than a larger one. Very often this problem has been solved by placing a focal point of the system at the surface in question. This is not very practical and often impossible and if the optical systems can be constructed without the need to take the dimension of the outer surface into consideration, one restricting parameter can be omitted, which is generally favourable to the system.

The invention overcomes the aforementioned problems. More particularly, the invention inhibits the effect of the very rapidly moving so-called ejector streams which are directed against said surface.

SUMMARY OF THE INVENTION

According to the present invention these streams are given such a direction near the surface of the optical object to be protected that they can be brought out through the tube by the gas supply. The device of the invention comprises a protective device with an opening placed in front of said surface, said inner walls extending out from said surface of said optical element when said optical element is placed in front of said surface, said protective device being positioned relative to said surface so as to define a slot extending peripherally around the edge of the opening facing said surface for forcing gas to stream through said slot, at least a part of the inner walls of the opening having an inwardly projecting part, said inwardly projecting part having a surface remote from said optical element which is parallel to or inclined outwardly from a symmetrical plane through said element.

DETAILED DESCRIPTION OF THE DRAWINGS

Figure 1:
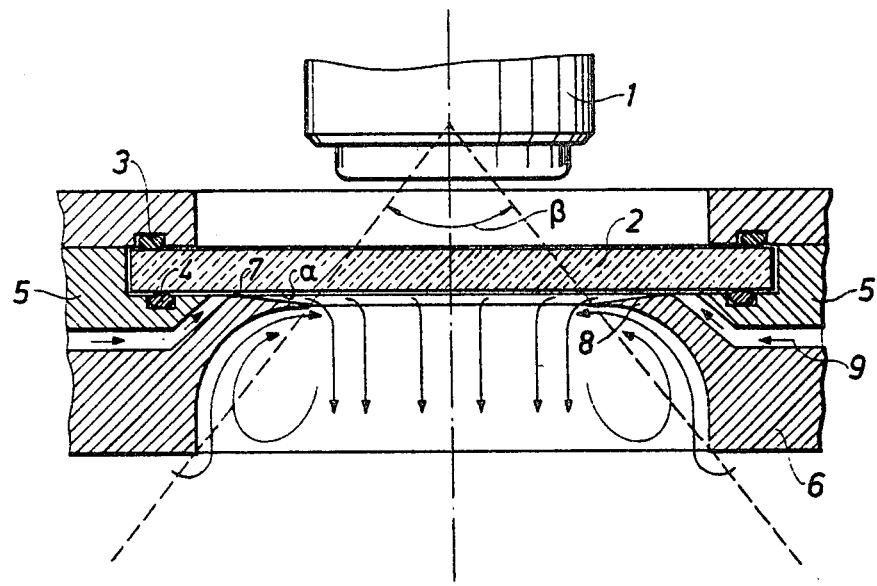
Figure 2:
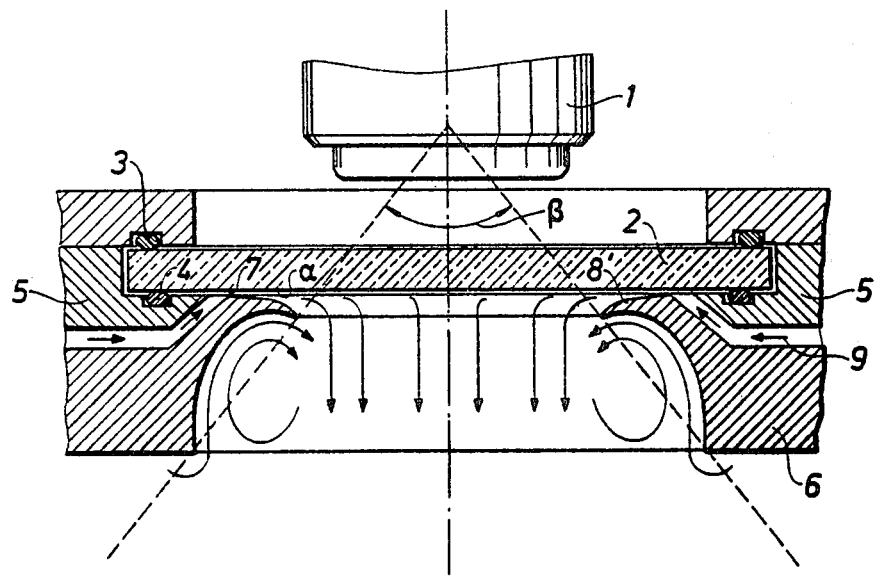
Figure 3A:
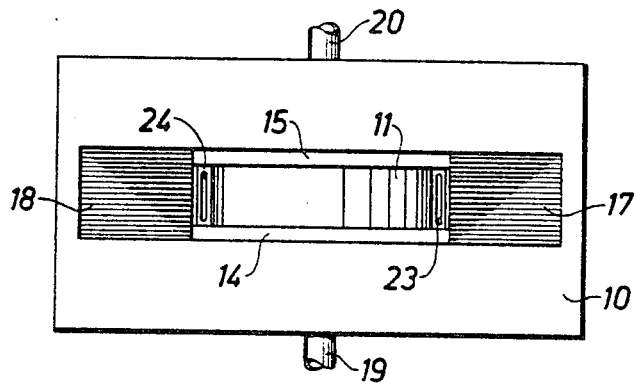
Figure 3B:
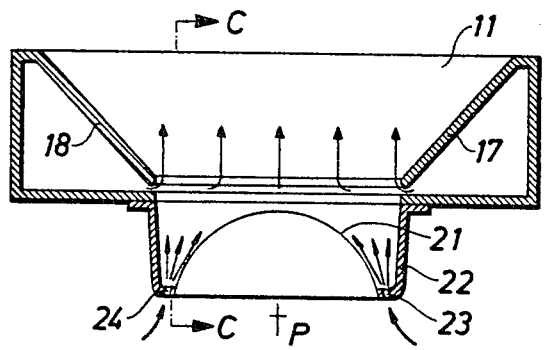
Figure 3C:
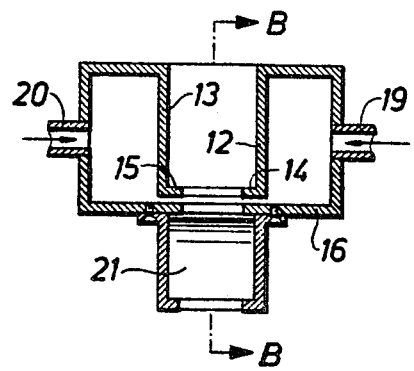

The characteristics of the present invention will be better understood by reading the following description of three embodiments thereof, given purely by way of example, and with reference to the accompanying drawings, in which:

FIGS. 1 and 2 are axial cross-sectional views through two embodiments provided for a planar window and FIGS. 3A to 3C are two axial cross-sectional veiws mutually turned through 90° to each other, through a third embodiment where the outer surface of the optical element to be protected is cylindrical.

In FIG. 1 an objective, for instance an IR-objective, is located in a protective environment on the inside of a planar window 2, which is sealingly mounted in the housing of an optical system including the objective, by means of sealing rings 3,4. In this case it is the outside of the window 2 which must be protected from dust, moisture etc., the outside of said window facing downwards in the Figure. In order to provide this protection, a protecting device 6, having an opening which may be of circular, oval or square configuration is placed in front of the window. In the embodiment shown in FIG. 1 the protecting device has an edge 7 placed in close proximity to the window, and from the edge a lip 8 protrudes inwardly into the opening. The edge 7 is placed only about a tenth of a millimeter from the window, thus allowing the gas to pass through the gas thus defined and giving an effective gas stream with a minimum of gas consumption. It is apparent that embodiments can be envisaged in which the edge 7 of the protective device is not placed close to the window, but instead close to a part holding the window, but since in the majority of cases said window - holding part extends some distance from the window, this would result in a greater gas consumption than when the edge is placed close to the window. The part of the lip 8 turned towards the window is planar and is inclined at an angle to the window, the apex of the angle being placed at the edge 7. Tests have shown that this angle must not be greater than 15°. The device 6 has also a surface which is inclined to the window on the side of the edge 7 remote from the opening, but close to the window, such that a restricted passage for the gas stream is provided immediately at the edge 7. Gas is fed towards the opening via a channel 9. Hence gas flows from the channel, via the narrow gap between the window 2 and the edge 7, over the edge of the lip 8 and out through the opening. It is suitable to cause the gas stream to be uniformly distributed around the entire edge 7, so that the gas streams meet symmetrically in the opening.

As shown in the Figure the edge of the lip 8 is placed at the limit of the field of view of the optical system. The opening has an inner wall which projects out from the window. The extent of this projection must be of such magnitude as to cause an essentially laminar flow of gas through the opening, at least in the vicinity of the window. The said inner wall is rounded outwardly from the lip 8 and at the edge of the lip is substantially parallel to the window, whilst at the outer part of the opening the inner wall is substantially perpendicular to the window. The outer edge of the opening is located just at the limit of the field view of the optics of the instrument, which field of view is illustrated in dash line in the Figure.

The purpose of the rounded form, which in the illustrated section is a quarter of a circle, is to ensure that those ejector-streams which are formed at the inner wall of the opening as a result of the gasflow at 9, partly because of the turbulence of the gas and partly because dust and moisture are sucked into the opening by the out-flowing gas, move across the window substantially parallel to the surface thereof. Consequently, it is possible to move the ejector streams away from the window by the gasflow 9. Experiments have shown that inwardly flowing ejector-streams obtain a velocity of such high magnitude that they readily pass straight through a curtain of flowing gas. Thus, if the ejector-streams move on to the window, dust and moisture will rapidly settle thereon. Experiments have shown that when the inner wall of the opening has a straight longitudinal section, i.e. when the inner wall is located substantially along the dash line in the Figures, the window quickly becomes dirty, despite the presence of a strong gas stream 9. The slope angle $\alpha$ between the lip 8 and the window 2 is also of importance in maintaining the window free from deposits. If this angle is larger than 15°, dirt etc, will be dposited on the window, in spite of the fact that the ejector-streams move parallel to the window. This is believed to be due to the fact that, at such a large angle, the expansion of the gas from the edge 7 to the edge of the lip is so large, that a turbulent flow occurs between the lip and the window. Hence, the angle $\alpha$ must be so small as to avoid such turbulent flow and to ensure that the gas flows over the edge of the lip 8 in a substantially laminar fashion. The edge is preferably made as sharp as possible, also in order to prevent turbulence and to ensure that as little dirt, moisture etc. as possible is deposited at the edge of the lip 8.

When carrying out operational tests with the embodiment illustrated in FIG. 1, the window was kept totally free from deposits, although inevitably a layer of dust and dirt was formed at the extension of the edge of the lip 8. This dirt layer will decrease the field of view of the objective. For the purpose of removing this layer, the velocity of the gas may be intermittently increased at given time intervals. The duration of these intervals, i.e. the length of time between consecutive increases in velocity, depends entirely upon the speed at which the layer builds up, and its thickness.

FIG. 2 illustrates a second embodiment of the device according to the invention, in which the lip 8' has a different form to the embodiment of FIG. 1. In this embodiment the surface of the lip 8' facing the window is curved essentially exponential. The other side of the lip 8' is also curved, such that the eject streams are directed along a path obliquely outwardly from the window when leaving the inner surface of the opening near the window. To this end the outer surface of the lip 8' is curved such as not to be parallel with the surface of the window. Thus, these ejector-streams are more easily brought out through the opening by the gas stream 9 than with the embodiment shown in FIG. 1. Naturally, the angle at which the side of the lip 8' facing the window slopes, must not be so large that turbulation occurs between the lip 8' and the window 2. It will be understood that the illustrated curvature of the sides of the lip 8' in FIG. 2 has been greatly exaggerated for the purpose of illustrating a principle and that a device whose lip 8' exhibited the illustrated magnitude of curvature would not function satisfactorily.

FIGS. 3A to 3C illustrate a further embodiment of the invention in which a nearly half-cylindrical surface of a protecting window of an optical system shall be protected.

FIG. 3A is a front view of the protective unit and FIGS. 3B and 3C are two sections mutually turned through 90° to each other. In this embodiment the protecting device includes a rectangular hollow box 10. In the front side an opening 11 is provided through the box, which opening is elongate and has its long sides parallel to the outer long sides of the box. The long side walls 12, 13 of the opening 11 are perpendicular to the front wall of the unit. Near the bottom side of the box, the long side walls of the opening 11 are bent inwardly such that a flange 14 projects perpendicular to the inner wall 12 and a flange 15 projects perpendicularly outwardly from the inner wall 13. An opening is provided in the bottom of the box 10 in register with the flanges 14 and 15. The narrow end walls 17 and 18 of the opening 11 are sloped, so that the opening is larger at the front side than at the bottom side, the slope being in register with the field of view of the optical system. The inner walls of the opening terminate at a short distance from the bottom 16, so that a narrow, peripherally extending slot is formed adjacent said bottom. Near the middle of the outer long side of the box 10 there are arranged two tubes 19 and 20, respectively, through which gas is supplied. This gas flows out through the slot near the bottom, and out through the opening 11.

Behind the opening 11 at the back of the box 10 there is arranged a semi-cyclindrical window 21. In this embodiment this window consists of a thin film 21 of polytetra fluorethene mounted in a holder (not shown). This unit is mounted on the rear side of a bathtube-formed housing, with the bottom omitted. The front side of the housing 22 is mounted on the rear side of the element 10, in such a way that the window 21 is located immediately below the opening 11, with its curvature facing the opening. In the bottom adjacent the narrow side of the housing 22, on each side of the window 21, there are provided slits 23, 24 which extend along said narrow side. Gas is blown through these slits 23, 24 in a manner such as to cause an overpressure in the space around the window 21. The scanning optics in this embodiment are placed behind the window 21 rotating around the center P of the circular form of the window. The narrow walls 17 and 18 of the opening 11 are placed where the scan has its side limits and are directed radially out from the window.

In this embodiment the purpose of the flanges 14 and 15 is to bend the ejector streams entering the opening 11 (from the outside) in towards the window, along the long sides of the opening, in such a way that said streams flow out essentially perpendicular to these long sides. The narrow sides 17 and 18 must not necessarily be bent or have a flange to bend the ejector-streams, since the distance from the inside ends of these sides to the window is so large that the ejector-streams can be bent, to go out through the opening 11, by the outstreaming gas from the box 10 and the overpressure around the window caused by the gas streams through the opening 23 and 24. Naturally, the narrow sides 17 and 18 can have a curved form, so that the ejector-streams coming out from these sides are parallel to the flanges 14 and 15, but this is not necessary in order for the protecting device to function satisfactorily. Essential in this embodiment are the flanges 14 and 15, because without them, dirt and dust etc. would quickly settle on the window 21. It is also essential that the box 10 is deep enough so that the gas flowing out of the opening 11 can be laminar. A deeper box will give a better result, and in use, a balance must be made between the result produced by the protecting device and its bulk. However, the depth of the opening 11 must not be below 1.5 times the width of the opening near the window 21.

The invention is not restricted to the described and illustrated embodiments, but can be modified within the scope of the claims.

We claim:

1. A device for keeping an outer surface of an optical element clean comprising a protective device with an opening placed in front of said surface, said opening having inner walls each having an inner and outer edge, said inner walls extending out from said surface of said optical element when said protective device is placed in front of said surface, said protective device being positioned relative to said surface so as to define a slot extending peripherally around the edge of the opening facing said surface, for forcing gas to stream through said slot, at least a part of the inner walls of the opening having a part projecting inwardly toward the axis of said optical element, said inwardly projecting part having a surface remote from said optical element which is parallel to or inclined outwardly from a symmetrical plane through said element, the surface of said inwardly projecting part facing said outer surface of the optical element and said outer surface defining at least a portion of said slot.

2. A device according to claim 1, wherein both the inner and the outer edge of said opening are essentially in register with the limit of the beam path for an optical system placed behind said optical element to be protected.

3. A device according to claim 1, wherein the inner walls of said opening are continually curved such that said walls at their outer edge are perpendicular to and at their inner edge are parallel to or inclined out from said symmetrical plane through said element to be protected.

4. A device according to claim 1, wherein said surface to be protected is strongly curved outwardly, said slot is placed in a plane going outside of said surface to be protected and an extra slot is provided at the edge of the said element through which gas is forced to stream outwardly.

5. A device according to claim 1, wherein said surface to be protected is a nearly half-cylindrical surface, said slot is placed in a plane going outside of said surface, said surface is placed in the bottom of a housing having walls extendng to the inner edge of said slot, and means are provided for blowing gas through said slot so as to build up an overpressure in relation to the surrounding atmosphere close to said surface to be protected.

6. A device according to claim 5, wherein an extra slot is provided at each side of the optical element and gas is forced to stream through said extra slots.

7. A device according to claim 4, wherein said inwardly projecting part is provided only at the end side part of the optical element to be protected.

* * * * *